United States Patent [19]
Thiel et al.

[11] Patent Number: 5,910,273
[45] Date of Patent: Jun. 8, 1999

[54] PROCESS FOR MANUFACTURING DENTAL PROSTHETICS BASED ON CERAMICS

[75] Inventors: Norbert Thiel; Gabriele Datzmann, both of Bad Sackingen, Germany

[73] Assignee: Vita Zahnfabrik H. Rauter GmbH & Co. KG, Bad Sackingen, Germany

[21] Appl. No.: 08/540,751

[22] Filed: Oct. 11, 1995

Related U.S. Application Data

[63] Continuation of application No. 08/157,541, Nov. 26, 1993, abandoned.

[30] Foreign Application Priority Data

Nov. 25, 1992 [DE] Germany .............................. 42 39 549
Dec. 12, 1992 [DE] Germany .............................. 42 42 007

[51] Int. Cl.⁶ .............................. A61C 13/00; A61C 13/08
[52] U.S. Cl. .............................. 264/16; 264/19; 264/643
[58] Field of Search .............................. 264/16, 17, 19, 264/20, 62, 67, 643

[56] References Cited

U.S. PATENT DOCUMENTS

| | | | |
|---|---|---|---|
| 4,894,609 | 1/1990 | Fujiki et al. | 324/107 |
| 5,009,709 | 4/1991 | Ibsen et al. | 106/35 |
| 5,250,352 | 10/1993 | Tyszblat | 428/306.6 |

FOREIGN PATENT DOCUMENTS

| | | |
|---|---|---|
| 0311214 | 4/1989 | European Pat. Off. . |
| 0455855 | 11/1991 | European Pat. Off. . |
| 0477157 | 3/1992 | European Pat. Off. . |
| 3015529 | 11/1980 | Germany . |
| 261741 | 11/1988 | Germany . |
| 4028187 | 3/1991 | Germany . |

OTHER PUBLICATIONS

Funkschau Artuell, vol. 18, 1986, p. 7, "Frankreich: Zahnersatz aus dem Computer".

Technik, Dental–Labor, vol. XXXV, Heft Apr. 1987, pp. 479–482, "Das Hi–Ceram–Verfahren Metallfreie Kronen auf einem Keramikgerüst".

*Primary Examiner*—Christopher A. Fiorilla
*Attorney, Agent, or Firm*—Jacobson, Price, Holman & Stern, PLLC

[57] ABSTRACT

A process for manufacturing dental prosthetics based on ceramics including the following steps:

- machine-processing a prefabricated shaped body to form a molded body with the patient's situation being considered, said prefabricated shaped body consisting of at least one oxide-ceramic material selected from the group consisting of aluminum oxide, magnesium oxide, zirconium oxide, and titanium oxide and minor amounts of siliceous additives;
- compacting the thus obtained molded body; and
- optionally jacketing the compacted molded body.

14 Claims, No Drawings

PROCESS FOR MANUFACTURING DENTAL PROSTHETICS BASED ON CERAMICS

This application is a continuation of application Ser. No. 08/157,541, filed Nov. 26, 1993, now abandoned.

BACKGROUND OF THE INVENTION

This invention is directed to a process for manufacturing dental prosthetics based on ceramics and a shaped body (green body) which may be used in this process.

In general, dental prosthetics are parts placed onto a patient's natural dentition to restore the latter with its natural functions as far as possible. These parts are manufactured in a highly expensive process. First, the dentist has to prepare or extract the part of dentition to be replaced, e.g., a single tooth or several teeth. After making a model, e.g., by preparing an impression using conventional procedures, the dentist or dental technician manufactures the appropriate denture, including crowns, bridges, inlays, and onlays.

In order to provide the dental prosthetics with an aesthetic appearance they may be jacketed with materials which have good mechanical properties and, at the same time, give the color sensation of natural teeth. As the material for jacketing denture or crowns etc., ceramics have proven to be particularly useful.

According to prior art, as the supports for the jacketing metal frameworks are possible which, in addition to the drawback of expensive and costly manufacturing, are intolerable for the patient at least in individual cases. Some of the drawbacks of restoration with metallic frameworks have been circumvented by the use of core materials made of ceramics.

Thus, EP 86,400,781.0 describes a process for manufacturing ceramic restorations such as bridges, crowns, inlays, onlays, etc., wherein initially, a master model is constructed. This model is coated and the thus obtained impression is cast with a special gypsum. A fine-grain oxide-ceramic slip is applied to the demolded gypsum framework, and the gypsum stump immediately withdraws the liquid proportion, and an almost dry mass layer is formed which may be processed quite well to give the desired framework. The obtained framework is sintered with the gypsum stump in a temperature range where shrinkage does not yet occur. In order to achieve high flexural strength, the porous framework is soaked with glass in an infiltration firing.

Here, processing is highly dependent on the dental technician's skill. In addition, subsequent processing of the framework is hardly possible due to its high mechanical strength and toughness.

Duret discloses the use of CAD/CAM methods for the construction and manufacturing of dental restorations. A prepared stump of tooth is recorded in its surrounding from various directions with a video camera. The recordings are digitalized and transferred via a CAD compatible computer in a three dimensional image. The dental restoration sitting to the above mentioned stump can be constructed online and visible on the screen according to models stored in the computer. Then the dental restoration is worked out by a computer assisted micromilling machine from a prefabricated block of the respective materials such as metal or dental ceramics. However, the material used, in the case of dental ceramics, does not show optimum mechanical strength.

DD 261,741 discloses a procedure which also forms inlays consisting of glass ceramic by mechanical treating. The mechanical treating can occur by aid of electro-optical scanning or contact milling. The glass ceramic to be used does not show the high mechanical strength which could be reached with materials known in the art but which materials cannot be treated mechanically with a reasonable expenditure because of their hardness.

SUMMARY OF THE INVENTION

Thus, it is the object of the present invention to devise a process by which dental prosthetics based on ceramics may be manufactured more economically, and wherein materials are employed in the form of green bodies which are produced on an industrial scale under optimum conditions. Thereby, the advantages of modern oxide-ceramic materials having high mechanical strength should also be exploited.

DETAILED DESCRIPTION

As the shaped bodies which may be employed in the process according to the invention, there may be mentioned green bodies, in particular, which have been manufactured from ceramics based on aluminum oxide, spinel, magnesium oxide, titanium oxide, zirconium oxide or combinations thereof and minor amounts of siliceous additives. The green bodies are manufacturable following the procedure as described in EP 86,400,781.

The manufacturing of the shaped bodies can be accomplished by casting, injecting or pressing the powdered ceramics into predetermined molds from which the corresponding slabs may be sintered to porosity. If the powdered material contains binder for better molding or forming the binder is preferably removed after forming by burning it out prior to sintering, for example, obtaining a prefabricated shaped body by injecting the powdered oxide material in a suitable mold, dry-pressing of the granulate obtained, optional removal of binder by burning out, and sintering. Thus, a) the dental restoration may be worked out directly and subsequently, may be compacted by glass infiltration, or b) the dental restoration may be compacted by glass infiltration and subsequently, the molded bodies may be worked out.

For better workability the shaped bodies (green bodies) are preferably provided with a fixation device, for example, a pin which is anchored in the shaped body and projecting over the surface of the shaped body. The pin can be put into the respective device of a contact milling apparatus so as to fix the shaped body during working.

Preferably, mechanical processing of the green body is effected by an abrasive and/or mill-cutting technique using a CAD/CAM supported process or by an abrasive copy process where it is possible to record the prepared teeth inside the mouth by photography or digitally or by conventional methods. In the conventional procedure, first, an impression is taken from the appropriately prepared tooth or dentition area, which then is copied directly or is digitalized by a laser and may be fed into a computer. The thus obtained data then serves in the computer-aided manufacturing of the dental prosthetics such as caps, inlays, onlays, and bridges, etc. which are accurately adapted to the patient's needs.

However, it is also possible to record the patient's situation by photographic registering and feeding appropriately digitalized data. Similarly, it is possible to directly take over the situation in the patient's mouth, for example, likewise by laser or contact copying. EP 0 455 855 discloses a device and process for the manufacturing of prosthetics and dental restorations. Such an approach is advantageous in that setting out from standardized material as is particularly represented by the industrially prefabricated green body, it is possible to directly manufacture the molded body for appropriate restoration, virtually perfectly adapted to the patient's situation, without going through those quite complex coating steps susceptible to faults, as are required in conventional dentistry.

Once the ceramics-based moldings adapted to the patient's situation have been mill-cut and ground, the moldings are treated with a glass melt. This is likewise done as described in EP 86,400,781.0. To this end, the glass is to possess the property of completely wetting the ceramics molding. The appropriate wetting properties of the glass may be varied by additives such as boron oxide, lead oxide or vanadium oxide. It is preferred to use such glasses where the expansion coefficient is below or near that of the ceramic molding so that satisfactory stability of the dental restoration to thermal shock is given. For example, infiltration is effected at about 1100° C. where the molten glass is able to permeate into the capillaries of the ceramics molding.

This may be followed by jacketing the infiltrated ceramics molding which, for instance, may be effected using one or multiple ceramics layers having different optical properties and tints so that the restoration may be given the appearance of natural teeth. of course, such process steps are likewise possible for partial restorations such as inlays, onlays, bridges, etc.

When using a CAD/CAM process, the process according to the invention permits a calculative basis for the ceramic jacketing to follow, e.g., using VITADUR α (dental porcelain for inlays, onlays, and facings). In particular, this is possible when using spinel as the ceramic core material. Also, moldings prepared in such fashion may then be jacketed by spraying known materials such as VITADUR (dental porcelains), -DENTIN (dentine porcelains), OPAK-DENTIN (opaque dentine porcelains) and -ENAMEL (enamel porcelains), using a spray-on system, and subsequent firing. In such a way, good mechanical values (infiltrated spinel: 300 to 400 MPa), natural translucence of the overall work, good fitting accuracy, and simple, rapid jacketing may be achieved.

On the whole, the process according to the invention permits the following advantages as compared to the prior art process, namely, outstanding processability of the porous molded body by machines, and high mechanical strength as evidenced by a three-point bending test subsequent to infiltration which, for infiltrated aluminum oxide is about from 450 to 500 MPa, and from 500 to 700 MPa for the combination of aluminum oxide/zirconium oxide. Thus, possible fields of use are single crown preparations within entire jaws, bridges in the front teeth and premolar areas where, in particular, an aesthetic appearance is important. Owing to the industrial prefabrication of the ceramic green bodies, possible individual errors associated with dentistry are largely avoided. The combination with jacketing ceramics provides a good aesthetic effect. With appropriately improved mechanical processing methods it is also possible to use green bodies already infiltrated according to the invention, and to mill-cut the appropriate restoration therefrom.

The entirety of everything cited above or below is hereby expressly incorporated herein by reference.

What is claimed is:

1. A process for manufacturing a dental prosthetic comprising the steps of:

forming a molded-body precursor of the prosthetic by machine-processing a porosity-sintered molded blank by CAD/CAM methods to accurately fit prepared definition according to data on a patient's dental situation, said porosity-sintered molded blank consisting essentially of at least one oxide-ceramic material selected from the group consisting of aluminum oxide, magnesium oxide, zirconium oxide, and titanium oxide and, optionally, a siliceous additive;

compacting the molded-body precursor by glass infiltration to form the prosthetic.

2. The process of claim 1 further comprising the step of either jacketing the molded-body precursor or jacketing the prosthetic.

3. The process of claim 2 wherein the data is obtained from dental impressions of the patient.

4. The process according to claim 2 wherein the data is directly registered on-line.

5. The process according to claim 2 wherein the prosthetic is selected from the group consisting of a bridge, a cap, an inlay, an onlay, a veneer, or a part thereof.

6. The method of claim 2 wherein the porosity-sintered molded blank is obtained by a method selected from the group consisting of form-molding and pressing, injection-molding, simultaneous form-molding and pressing, and press-molding a composition comprising a powder of the at least one oxide-ceramic material.

7. The method of claim 2 wherein the porosity-sintered molded blank is obtained by a process comprising the steps of (a) injection-molding a powder of the at least one oxide-ceramic material, optionally combined with a binder followed by removing the binder after injection-molding, to form a green body and (b) porosity-sintering the green body.

8. The method of claim 2 wherein the porosity-sintered molded blank is obtained by a process comprising the steps of (a) dry-pressing granulates of the at least one oxide ceramic material, optionally combined with a binder followed by removal of the binder after dry-pressing, to form a green body and (b) porosity-sintering the green body.

9. The process of claim 1 wherein the data is obtained from dental impressions of the patient.

10. The process according to claim 1 wherein the data is directly registered on-line.

11. The process according to claim 1 wherein the prosthetic is selected from the group consisting of a bridge, a cap, an inlay, an onlay, a veneer, or a part thereof.

12. The method of claim wherein the porosity-sintered molded blank is obtained by a method selected from the group consisting of form-molding and pressing, injection-molding, simultaneous form-molding and pressing, and press-molding a composition comprising a powder of the at least one oxide-ceramic material.

13. The method of claim 1 wherein the porosity-sintered molded blank is obtained by a process comprising the steps of (a) injection-molding a powder of the at least one oxide-ceramic material, optionally combined with a binder followed by removing the binder after injection-molding, to form a green body and (b) porosity-sintering the green body.

14. The method of claim 1 wherein the porosity-sintered molded blank is obtained by a process comprising the steps of (a) dry-pressing granulates of the at least one oxide ceramic material, optionally combined with a binder followed by removal of the binder after dry-pressing, to form a green body and (b) porosity-sintering the green body.

* * * * *